United States Patent
Gebert-Schwarzwaelder et al.

(10) Patent No.: US 9,827,180 B2
(45) Date of Patent: *Nov. 28, 2017

(54) AGENTS FOR OXIDATIVELY DYEING HAIR, CONTAINING SPECIFIC COMBINATIONS OF DEVELOPERS AND COUPLERS

(71) Applicant: Henkel AG & Co. KGaA, Duesseldorf (DE)

(72) Inventors: Antje Gebert-Schwarzwaelder, Neuss (DE); Astrid Kroos, Monheim (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/153,825

(22) Filed: May 13, 2016

(65) Prior Publication Data

US 2016/0250124 A1    Sep. 1, 2016

Related U.S. Application Data

(63) Continuation of application No. PCT/DE2014/200598, filed on Oct. 28, 2014.

(30) Foreign Application Priority Data

Dec. 6, 2013   (DE) .................. 10 2013 225 193

(51) Int. Cl.
| | | |
|---|---|---|
| *A61Q 5/10* | (2006.01) | |
| *A61K 8/49* | (2006.01) | |
| *A61K 8/34* | (2006.01) | |
| *A61K 8/41* | (2006.01) | |
| *A61K 8/22* | (2006.01) | |
| *A61Q 5/08* | (2006.01) | |
| *B65D 81/32* | (2006.01) | |

(52) U.S. Cl.
CPC .............. *A61K 8/494* (2013.01); *A61K 8/22* (2013.01); *A61K 8/347* (2013.01); *A61K 8/411* (2013.01); *A61K 8/415* (2013.01); *A61K 8/4913* (2013.01); *A61Q 5/08* (2013.01); *A61Q 5/10* (2013.01); *B65D 81/32* (2013.01); *A61K 2800/4324* (2013.01); *A61K 2800/88* (2013.01)

(58) Field of Classification Search
CPC .......... A61Q 5/10; A61K 8/347; A61K 8/415; A61K 8/22; A61K 8/494; A61K 8/4953; A61K 2800/88

See application file for complete search history.

(56) References Cited

U.S. PATENT DOCUMENTS

| | | | |
|---|---|---|---|
| 2003/0192131 A1 | 10/2003 | Audousset | |
| 2004/0221398 A9 | 11/2004 | Audousset | |
| 2006/0059633 A1 | 3/2006 | Audousset | |
| 2009/0119852 A1* | 5/2009 | Marsh ...................... | A61K 8/34 8/408 |

FOREIGN PATENT DOCUMENTS

DE    102005052139 A1    5/2007

OTHER PUBLICATIONS

PCT International Search Report (PCT/DE2014/200598) dated May 5, 2015.
Database GNPD Mintel, "Permanent Hair Colour Cream", XP002735467, Database Accession No. 1151993, 2009.

* cited by examiner

*Primary Examiner* — Eisa Elhilo
(74) *Attorney, Agent, or Firm* — David K. Benson

(57) ABSTRACT

Agents for oxidatively dyeing of keratinic fibers include in a cosmetic carrier, (A) as a developer, 4,5-diamino-1-(2-hydroxyethyl)-1H-pyrazole and/or one of the physiologically acceptable salts thereof, (B) as a developer, p-aminophenol and/or one of the physiologically acceptable salts thereof, (C) as a coupler, 2,6-bis(2'-hydroxyethylamino)-1-methylbenzene and/or one of the physiologically acceptable salts thereof, and (D) as a coupler, at least one m-dihydroxybenzene derivative from the group consisting resorcinol, 2-methylresorcinol and/or 4-chlororesorcinol as coupler.

11 Claims, No Drawings

AGENTS FOR OXIDATIVELY DYEING HAIR, CONTAINING SPECIFIC COMBINATIONS OF DEVELOPERS AND COUPLERS

FIELD OF THE INVENTION

The present invention generally relates to an agent for oxidatively dyeing keratinic fibers, in particular hair, which includes a specific combination of oxidation dye precursors.

BACKGROUND OF THE INVENTION

Changing the color of keratinic fibers, in particular hair, represents an important area of modern cosmetics. The appearance of the hair may thus be adapted to current fashion trends and to the person's individual preferences. Various options are known to those skilled in the art for changing the color of the hair. The hair color may be temporarily changed by using direct dyes. In the process, dyes which are already formed diffuse from the coloring agent into the hair fiber. Although coloration using direct dyes involves little damage to the hair, it is disadvantageous that the colorings obtained with direct dyes are not very durable and wash out quickly.

If the user desires a long-lasting color result or a shade that is lighter than his/her original hair color, oxidative color-changing agents are customarily used. For long-lasting, intense colorations having appropriate fastness properties, so-called oxidation dyes are used. Such coloring agents customarily include oxidation dye precursors, so-called developer components and coupler components, which form the actual dyes with one another under the influence of oxidizing agents. Oxidation dyes are characterized by long-lasting color results.

Extensive prior art already exists with regard to oxidative coloring agents. Considerable testing has been conducted, in particular for optimizing the fastness properties of the colorings that are achievable with these agents.

However, despite the large number of optimization tests already carried out, there is still a need for improvement of the fastness properties of oxidatively dyed keratin fibers, in particular when they are colored in a shade of red. In particular the wash fastness of shades of red, copper and violet cannot yet be considered to be optimal.

It is therefore desirable to provide oxidative coloring agents for achieving shades of red, violet, and copper having improved wash fastness.

The wash fastness of a color shade is understood to mean the change in color of the hair strands colored with this shade under the influence of multiple hair washings. This change in color may involve a shift of the color toward another hue, or also lightening of the coloring. Both changes in color are equally undesirable to the user. Color shades with good wash fastness experience little or no change in color, even after repeated hair washings. The hair washing may take place using a shampoo, a conditioning shampoo, or a conditioner.

Furthermore, other desirable features and characteristics of the present invention will become apparent from the subsequent detailed description of the invention and the appended claims, taken in conjunction with this background of the invention.

BRIEF SUMMARY OF THE INVENTION

The present invention is directed to an agent for oxidatively dyeing keratinic fibers that includes 4,5-diamino-1-(2-hydroxyethyl)-1H-pyrazole as the first developer, p-aminophenol as the second developer, 2,6-bis(2'-hydroxyethylamino)-1-methylbenzene as the first coupler, and at least one derivative of m-dihydroxybenzene as the second coupler. The present invention further relates to a multicomponent packaging unit which includes the above-mentioned agent, and use of the agent for improving the wash fastness of oxidative colorings.

Accordingly, an agent for oxidatively dyeing keratinic fibers includes in a cosmetic carrier 4,5-diamino-1-(2-hydroxyethyl)-1H-pyrazole and/or one of the physiologically acceptable salts thereof as developer; p-aminophenol and/or one of the physiologically acceptable salts thereof as developer; 2,6-bis(2'-hydroxyethylamino)-1-methylbenzene and/or one of the physiologically acceptable salts thereof as coupler; and at least one m-dihydroxybenzene derivative from the group comprising resorcinol, 2-methylresorcinol, and/or 4-chlororesorcinol as coupler.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now surprisingly been found that keratinic fibers, in particular hair, have excellent wash fastness when they are dyed with agents that include a specific combination of two certain oxidation dye precursors of the developer type and two certain oxidation dye precursors of the coupler type.

The present invention relates firstly to an agent for oxidatively dyeing keratinic fibers, which includes in a cosmetic carrier (A) 4,5-diamino-1-(2-hydroxyethyl)-1H-pyrazole and/or one of the physiologically acceptable salts thereof as developer, (B) p-aminophenol and/or one of the physiologically acceptable salts thereof as developer, (C) 2,6-bis(2'-hydroxyethylamino)-1-methylbenzene and/or one of the physiologically acceptable salts thereof as coupler, and (D) at least one m-dihydroxybenzene derivative from the group comprising resorcinol, 2-methylresorcinol, and/or 4-chlororesorcinol as coupler.

Keratinic fibers, keratin-containing fibers, or keratin fibers are understood to mean fur, wool, feathers, and in particular human hair. Although the agents according to the invention are primarily suited for lightening and dyeing keratin fibers, use in other fields is also possible in principle.

The agents include the oxidation dye precursors essential to the invention in each case in a cosmetic carrier, preferably in a suitable aqueous, alcoholic, or aqueous-alcoholic carrier. For purposes of the oxidative change in color, such carriers may be, for example, creams, emulsions, gels, or also surfactant-containing foaming solutions such as shampoos, foam aerosols, foam formulations, or other preparations that are suitable for application to the hair. Agents for oxidatively dyeing keratinic fibers are particularly preferably creams or emulsions.

The content of oxidation dye precursors of developer type (A) and (B) in the agents and the content of oxidation dye precursors of coupler type (C) and (D) in the agents is characterizing for the agents according to the invention.

Within the meaning of the present invention, a developer is understood to mean an oxidation dye precursor of the developer type. Within the meaning of the present invention, a coupler is understood to mean an oxidation dye precursor of the coupler type.

As the first oxidation dye precursor of developer type (A), the agents according to the invention include 4,5-diamino-1-(2-hydroxyethyl)-1H-pyrazole and/or one of the physiologically acceptable salts thereof 4,5-Diamino-1-(2-hydroxyethyl)-1H-pyrazole is the compound of formula (I):

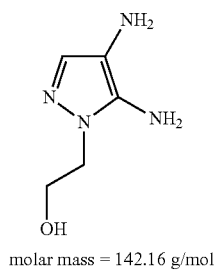

(I)

molar mass = 142.16 g/mol

Preferred physiologically acceptable salts of 4,5-diamino-1-(2-hydroxyethyl)-1H-pyrazole are in particular the hydrochlorides (monohydrochloride×HCl, or dihydrochloride×2 HCl), the sulfate (×H2SO4), and the hydrobromides (monohydrobromide×HBr, or dihydrobromide×2 HBr) of the compound. 4,5-Diamino-1-(2-hydroxyethyl)-1H-pyrazole sulfate (formula (Ia)) is very particularly preferred:

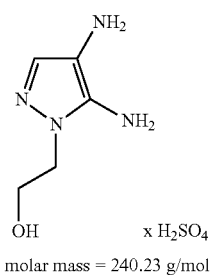

(Ia)

molar mass = 240.23 g/mol

As the second oxidation dye precursor of developer type (B), the agents according to the invention include p-aminophenol and/or one of the physiologically acceptable salts thereof p-Aminophenol is a compound of formula (II)

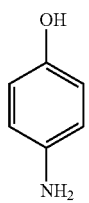

(II)

molar mass = 109.13 g/mol

Preferred physiologically acceptable salts of p-aminophenol are in particular the hydrochloride (monohydrochloride× HCl), the hemisulfate (×½ H2SO4) and the hydrobromide (monohydrobromide×HBr) of the compound. p-Aminophenol is more preferably used in the form of the hydrochoride (IIa) thereof.

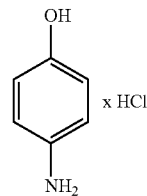

(IIa)

molar mass = 145.59 g/mol

As the first oxidation dye precursor of coupler type (C), the agents according to the invention include 2,6-bis(2'-hydroxyethylamino)-1-methylbenzene and/or one of the physiologically acceptable salts thereof 2,6-bis(2'-hydroxyethylamino)-1-methylbenzene is the compound of formula (III):

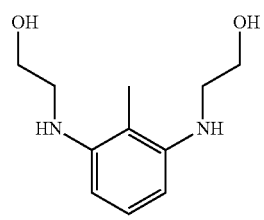

(III)

molar mass = 210.28 g/mol

Preferred physiologically acceptable salts of 2,6-bis(2'-hydroxyethylamino)-1-methylbenzene are in particular the hydrochlorides (monohydrochloride×HCl, or dihydrochloride×2 HCl), the sulfate (×H2SO4) and the hydrobromides (monohydrobromide×HBr, or dihydrobromide×2 HBr) of the compound. 2,6-bis(2'-hydroxyethylamino)-1-methylbenzene is particularly preferably used, not in the salt form, but, rather, in the form of the free compound (i.e. as the compound of formula (III)).

As the second oxidation dye precursor of coupler type (D), the agents according to the invention include at least one m-dihydroxybenzene derivative from the group comprising resorcinol, 2-methylresorcinol, and/or 4-chlororesorcinol. Resorcinol is the compound of formula (IV), 2-methylresorcinol is the compound of formula (V), and 4-chlororesorcinol is the compound of formula (VI).

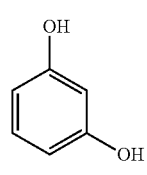

(IV)

molar mass = 110.11 g/mol

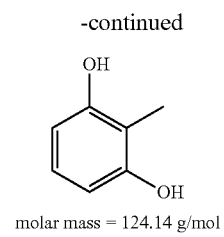

molar mass = 124.14 g/mol

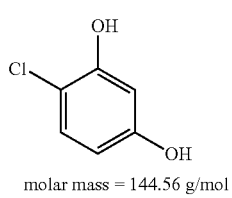

molar mass = 144.56 g/mol

In the course of the studies leading to the present invention, it has been found that using a combination of the four different oxidation dye precursors (A), (B), (C), and (D), compared to using only three oxidation dye precursors (for example, (A), (C), and (D) or (A), (B), and (C), etc.) in oxidative coloring agents results in improved wash fastness.

In this regard, it has found to be particularly preferable when the oxidation dye precursors are used in the agents in specific molar ratios relative to one another.

The molar mass (units: g/mol) of a compound is defined as the mass (units: g) per substance quantity (units: mol).

During the oxidative dyeing process, in each case one molecule of an oxidation dye precursor of the developer type reacts with one or more molecules of the oxidation dye precursors of the coupler type. It has been found that high color intensities and good fastness properties may be achieved when the substance quantities of the dye precursors reacting with one another (i.e., their molar quantities) are coordinated particularly well with one another.

The substance quantity is understood to mean the quantity of a material portion, based on the number of particles respectively included therein. The substance quantity is expressed in the base units of moles (mol or mmol).

The molar quantity of the oxidation dye precursor included in a coloring agent may be obtained by dividing the quantity used by its molar quantity. Example:
100 g of a color cream includes
(A) (4.80 g of 4,5-diamino-1-(2-hydroxyethyl)-1H-pyrazole sulfate
Molar mass of 4,5-diamino-1-(2-hydroxyethyl)-1H-pyrazole sulfate=240.23 g/mol The molar quantity of the 4,5-diamino-1-(2-hydroxyethyl)-1H-pyrazole sulfate included in the agent (100 g) is (4.80 g/[240.23 g/mol])=0.020 mol (corresponds to 20.0 mmol).

Advantageous effects on the wash fastness of the colorings which are achievable with these agents may be observed in particular when the developers from group (A) are used in the agents in a molar excess with respect to the developers from group (B), i.e., when the molar ratio (A)/(B) has a value greater than 1. The ratio preferably has a value of at least 1.2, more preferably at least 1.4, even more preferably at least 1.6, and particularly preferably at least 1.8.

The basis for calculating the molar ratio (A)/(B) is the total molar quantity of all developers of group (A) included in the agent (i.e., the molar quantity of 4,5-diamino-1-(2-hydroxyethyl)-1H-pyrazole plus the molar quantities of its salts), which is set in a relation with the total molar quantity of all developers of group (B) included in the agent (i.e., the molar quantity of p-aminophenol plus the molar quantities of its salts).

A very particularly preferred agent for oxidatively dyeing keratinic fibers is characterized in that the molar ratio of all developers of group (A) included in the agent to all developers of group (B) included in the agent, i.e., the molar ratio (A)/(B), has a value of at least 1, preferably at least 1.2, more preferably at least 1.4, even more preferably at least 1.6, and particularly preferably at least 1.8.

The oxidative coloring agents which include the developers from group (A) and the developers from group (B) in a molar ratio of 1.8 to 2.2 have the best fastness properties. However, if the molar ratio of (A)/(B) further increases to values greater than 3, there is a tendency once again toward degradation of the wash fastness of the colorings obtained with these agents. For this reason, it is advantageous for the molar ratio (A)/(B) not to exceed values of 3.

A very particularly preferred agent for oxidatively dyeing keratinic fibers is characterized in that the molar ratio of all developers of group (A) included in the agent to all developers of group (B) included in the agent, i.e., the molar ratio (A)/(B), has a value of 3 maximum, preferably 2.8 maximum, more preferably 2.6 maximum, even more preferably 2.4 maximum, and particularly preferably 2.2 maximum.

Example:
100 g of a color cream includes
(A) 4.80 g of 4,5-diamino-1-(2-hydroxyethyl)-1H-pyrazole sulfate.
The molar quantity of the (4,5-diamino-1-(2-hydroxyethyl)-1H-pyrazole sulfate) included in the agent (100 g) is (4.80 g/[240.23 g/mol])=0.020 mol (corresponding to 20.0 mmol)
(B) g p-aminophenol (hydrochloride)
The molar quantity of the p-aminophenol (hydrochloride) included in the agent (100 g) is (1.46 g/[145.59 g/mol])=0.010 mol (corresponding to 10.0 mmol)
The molar ratio (A)/(B) has a value of (0.020 mol)/(0.010 mol)=2.

As the first oxidation dye precursor of coupler type (C), the agents according to the invention include 2,6-bis(2'-hydroxyethylamino)-1-methylbenzene and/or one of the physiologically acceptable salts thereof.

As the second oxidation dye precursor of coupler type (D), the agents according to the invention include at least one m-dihydroxybenzene derivative from the group comprising resorcinol, 2-methylresorcinol, and/or -4-chlororesorcinol Each of the couplers from group (D) has proven to be very preferably suitable with regard to optimizing the fastness properties.

In another very particularly preferred embodiment, an agent according to the invention for oxidatively dyeing keratinic fibers is therefore characterized in that it includes (D) 2-methylresorcinol as coupler.

In another very particularly preferred embodiment, an agent according to the invention for oxidatively dyeing keratinic fibers is therefore characterized in that it includes (D) resorcinol as coupler.

In another very particularly preferred embodiment, an agent according to the invention for oxidatively dyeing keratinic fibers is therefore characterized in that it includes (D) 4-chlororesorcinol as coupler.

In another embodiment it is likewise preferred when the agents according to the invention include at least two oxidation dye precursors of the coupler type from group (D).

Also preferred is an agent for oxidatively dyeing keratinic fibers, that include in a cosmetic carrier (A) 4,5-diamino-1-(2-hydroxyethyl)-1H-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) resorcinol and 2-methylresorcinol as coupler.

Also preferred is an agent for oxidatively dyeing keratinic fibers, that include in a cosmetic carrier
(A) 4,5-diamino-1-(2-hydroxyethyl)-1H-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) resorcinol and 4-chlororesorcinol as coupler.

Also preferred is an agent for oxidatively dyeing keratinic fibers, that include in a cosmetic carrier
(A) 4,5-diamino-1-(2-hydroxyethyl)-1H-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) 2-methylresorcinol and 4-chlororesorcinol as coupler.

In another embodiment it is likewise preferred when the agents according to the invention include all three oxidation dye precursors of the coupler type from group (D).

Furthermore, also preferred is an agent for oxidatively dyeing keratinic fibers, that include in a cosmetic carrier
(A) 4,5-diamino-1-(2-hydroxyethyl)-1H-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) resorcinol, 2-methylresorcinol, and 4-chlororesorcinol as coupler.

In tests conducted for the present invention, it was also found that the molar ratio of the couplers from groups (C) and (D) relative to one another may also have a great influence on the fastness properties. The best wash fastness was observed when the couplers from group (C) and the couplers from group (D) were used in approximately equimolar quantities, i.e., when the ratio (C)/(D) had a value equal or close to 1.

The basis for calculating the molar ratio (C)/(D) is the total molar quantity of all couplers of group (C) included in the agent (i.e., the molar quantity of 2,6-bis(7'-hydroxyethylamino)-1-methylbenzene plus the molar quantities of its salts), which is set in a relation with the total molar quantity of all couplers of group (D) included in the agent (i.e., the sum of the molar quantities of resorcinol, 2-methylresorcinol, and 4-chlororesorcinol). At least one compound from group (D) comprising resorcinol, 2-methylresorcinol, and 4-chlororesorcinol must be included in the agent according to the invention.

In another very particularly preferred embodiment, an agent according to the invention for oxidatively dyeing keratinic fibers is therefore characterized in that the molar ratio of all couplers of group (C) included in the agent to all couplers of group (D) included in the agent, i.e., the molar ratio (C)/(D), has a value of at least 0.5, preferably at least 0.6, more preferably at least 0.7, and particularly preferably at least 0.8.

In another very particularly preferred embodiment, an agent according to the invention for oxidatively dyeing keratinic fibers is further characterized in that the molar ratio of all couplers of group (C) included in the agent to all couplers of group (D) included in the agent, i.e., the molar ratio (C)/(D), has a value of 1.5 maximum, preferably 1.4 maximum, more preferably 1.3 maximum, and particularly preferably 1.2 maximum.

For application-related reasons as well as toxicological reasons, the couplers are used in a slight molar excess in the ratio with respect to the developers. The best results have been obtained when the molar ratio of all developers of groups (A) and (B) included in the agent to all couplers of groups (C) and (D) included in the agent, i.e., the molar ratio [(A)+(B)]/[(C)+(D)], has a value of approximately 0.75, which means that for 3 molar portions of developers [(A)+(B)], approximately 4 molar portions of couplers [(C)+(D)] are used. Similarly good results have been obtained within a variation range; i.e., the fastness values were excellent even when the molar ratio [(A)+(B)]/[(C)+(D)] had values between 0.65 and 0.80. In addition, it was possible to avoid skin irritations while maintaining these molar ratios.

In another very particularly preferred embodiment, an agent according to the invention for oxidatively dyeing keratinic fibers is therefore characterized in that the molar ratio of all developers of groups (A) and (B) included in the agent to all couplers of groups (C) and (D) included in the agent, i.e., the molar ratio [(A)+(B)]/[(C)+(D)], has a value of at least 0.4, preferably at least 0.5, more preferably at least 0.6, and particularly preferably at least 0.65.

In another very particularly preferred embodiment, an agent according to the invention for oxidatively dyeing keratinic fibers is therefore characterized in that the molar ratio of all developers of groups (A) and (B) included in the agent to all couplers of groups (C) and (D) included in the agent, i.e., the molar ratio [(A)+(B)]/[(C)+(D)], has a value of 0.95 maximum, preferably 0.90 maximum, more preferably 0.85 maximum, and particularly preferably 0.80 maximum.

The basis for calculating the molar ratio [(A)+(B)]/[(C)+(D)] is analogous to the above-mentioned calculations of the total molar quantity of all developers from groups (A) and (B) included in the agent, which are set in a relation with the total molar quantity of all couplers from groups (C) and (D) included in the agent.

The ready-to-apply oxidative coloring agent is prepared shortly before application by mixing two (or more) different components.

The first component is color preparation (K1), which is preferably set alkaline, and which includes the oxidation dye precursors (A), (B), (C), and (D) (and optionally even further additional oxidation dye precursors and/or further direct dyes). This color preparation is mixed with an oxidizing agent preparation (K2) prior to application. For stability reasons, the oxidizing agent preparation (K2) is preferably set to an acidic pH, and includes the oxidizing agent. The oxidizing agent is usually hydrogen peroxide, which is used in the form of its aqueous solution.

The components (K1) and (K2) may be combined with one another in different weight ratios from 1:3 to 3:1, resulting in the ready-to-apply oxidative coloring agent. The components (K1) and (K2) are preferably mixed together in a quantity ratio of 1:1.

All oxidation dye precursors are included in color preparation (K1); therefore, all statements concerning weight quantities, weight ratios, molar quantities, molar ratios, and molalities of the oxidation dye precursors refer to the overall quantity of color preparation (K1).

It has now been found to be advantageous when the agents according to the invention for oxidatively dyeing keratin fibers preferably include the developers of group (A) in a certain overall molality.

The overall molality is understood to mean the total molar quantity of all developers from group (A) included in the oxidative coloring agent; this overall molality refers to the total molar quantity of the developers (A) in the total weight of color preparation (K1) (units: mol developer (A) per kg of color preparation (K1).

In another very particularly preferred embodiment, an agent according to the invention for oxidatively dyeing keratinic fibers is therefore characterized in that it includes the developer(s) of group (A) in an overall molality of 0.10 to 0.50 mol/kg, preferably 0.15 to 0.45 mol/kg, more preferably 0.16 to 0.40 mol/kg, and particularly preferably 0.18 to 0.35 mol/kg, based on the total weight of the agent.

Since all the oxidation dye precursors are present in color preparation (K1), the total weight of the above-mentioned agent is understood to mean the total weight of color preparation (K1). Color preparation (K1), which particularly preferably includes the developers of group (A) in an overall molality of 0.18 to 0.35 mol/kg, is then mixed with oxidizing agent preparation (K2) prior to application. For a mixing ratio (K1)/(K2) of 1:1, the resulting ready-to-apply oxidative coloring agent consequently includes the developers from group (A) in an overall molality of 0.090 to 0.175 mol/kg.

The couplers of groups (C) and (D) are likewise particularly preferably included in certain overall molalities in the agent according to the invention. Colorings with excellent fastness properties have been obtained when the couplers are used within these preferred quantity ranges.

The overall molality is understood to mean the total molar quantity of all couplers from groups (C) and (D) included in the oxidative coloring agent; the overall molality refers to the total molar quantity of couplers (C) and (D) in the total weight of color preparation (K1) (units: mol couplers [(C)+ (D)] per kg of color preparation (K1).

In another very particularly preferred embodiment, an agent according to the invention for oxidatively dyeing keratinic fibers is therefore characterized in that it includes the couplers of groups (C) and (D) in an overall molality of 0.10 to 1.00 mol/kg, preferably 0.20 to 0.90 mol/kg, more preferably 0.30 to 0.80 mol/kg, and particularly preferably 0.40 to 0.70 mol/kg, based on the total weight of the agent.

Since all the oxidation dye precursors are present in color preparation (K1), the total weight of the above-mentioned agent is understood to mean the total weight of color preparation (K1). For further shading, the agents according to the invention (i.e., color preparation (K1)) may additionally include even further oxidation dye precursors of the developer type and/or of the coupler type which are different from the developers and couplers from groups (A), (B), (C), and (D).

Preferred additional oxidation dye precursors of the developer type may be selected from the group comprising p-phenylenediamine, p-toluylenediamine, 2-(1,2-dihydroxyethyl)-p-phenylenediamine, N,N-bis-(2-hydroxyethyl)-p-phenylenediamine, 2-(2,5-diaminophenyl)ethanol, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-amino-phenyl)methane, 1,3-bis-(2,5-diaminophenoxy)propan-2-ol, N,N'-bis-(4-aminophenyl)-1,4-diaza-cycloheptane, 1,10-bis-(2,5-diaminophenyl)-1,4,7,10-tetraoxadecane, p-aminophenol, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

However, in one particularly preferred embodiment the agent according to the invention includes no further oxidation dye precursors of the developer type.

Also preferred is an agent for oxidatively dyeing keratinic fibers, that include in a cosmetic carrier
(A) 4,5-diamino-1-(2-hydroxyethyl)-1H-pyrazole as developer and/or one of the physiologically acceptable salts thereof,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) at least one m-dihydroxybenzene derivative from the group comprising resorcinol, 2-methylresorcinol, and/or 4-chlororesorcinol as coupler,
with the condition that the agent includes no further developers besides the developers from groups (A) and (B).

Also preferred is an agent for oxidatively dyeing keratinic fibers, that include in a cosmetic carrier
(A) 4,5-diamino-1-(2-hydroxyethyl)-IH-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) at least one m-dihydroxybenzene derivative from the group comprising resorcinol, 2-methylresorcinol, and/or 4-chlororesorcinol as coupler,
with the condition that the agent includes no compound from the group comprising p-phenylenediamine, p-toluylenediamine, N,N-bis-(2-hydroxyethyl)-p-phenylenediamine, 2-(2,5-diaminophenyl)ethanol, 2-methoxymethylphenylenediamine, p-aminophenol, 4-amino-2-aminomethylphenol, 2,4,5,6-tetraaminopyrimidine, 4-hydroxy-2,5,6-triaminopyrimidine, and 2-hydroxy-4,5,6-triaminopyrimidine.

Also preferred is an agent for oxidatively dyeing keratinic fibers, that include in a cosmetic carrier
(A) 4,5-diamino-1-(2-hydroxyethyl)-IH-pyrazole and/or one of the physiologically acceptable salts thereof as developer,
(B) p-aminophenol and/or one of the physiologically acceptable salts thereof as developer,
(C) 2,6-bis(2'-hydroxyethylamino)-1-methylbenzene and/or one of the physiologically acceptable salts thereof as coupler, and
(D) at least one m-dihydroxybenzene derivative from the group comprising resorcinol, 2-methylresorcinol, and/or 4-chlororesorcinol as coupler,
with the condition that the agent includes no compound from the group comprising p-phenylenediamine, p-toluylenediamine, N,N-bis-(2-hydroxyethyl)-p-phenylenediamine, 2-methoxymethyl-p-phenylenediamine, p-aminophenol, 4-amino-aminomethylphenol, 2,4,5,6-tetraaminopyrimidine, 4-hydroxy-2,5,6-triaminopyrimidine, and 2-hydroxy-4,5,6-triaminopyrimidine.

Coupler components which may additionally be included are preferably selected from one of the following classes: m-aminophenol, o-aminophenol, m-diaminobenzene, o-diaminobenzene, and/or the derivatives thereof; naphthalene derivatives that include at least one hydroxy group; trihydroxybenzene derivatives; pyridine derivatives; pyrimidine derivatives; indole derivatives, and indoline derivatives; pyrazolone derivatives (1-phenyl-3-methylpyrazol-5-one, for example); morpholine derivatives (6-hydroxybenzomorpholine or 6-aminobenzomorpholine, for example); quinoxaline derivatives (6-methyl-1,2,3-tetrahydroquinoxaline, for example), and mixtures of two or more compounds of one or more of these classes.

Preferred m-aminophenol coupler components are selected from at least one compound from the group, formed by m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts thereof. Preferred m-diaminobenzene coupler components are selected from at least one compound from the group comprising m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, and the physiologically acceptable salts thereof. Preferred o-diaminobenzene coupler components are selected from at least one compound from the group formed by 3,4-diaminobenzoic acid and 2,3-diamino-1-methylbenzene, and the physiologically acceptable salts thereof. Preferred naphthalene derivatives that include at least one hydroxy group are selected from at least one compound of the group comprising 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred trihydroxybenzenes and the derivatives thereof are selected from at least one compound of the group comprising pyrogallol and 1,2,4-trihydroxybenzene. Preferred pyridine derivatives are selected from at least one compound of the group comprising 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof. Preferred pyrimidine derivatives are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and the physiologically acceptable salts thereof. Preferred indole derivatives are selected from at least one compound from the group formed by 4-hydroxyindole, 6-hydroxyindole, and 7-hydroxyindole, and the physiologically acceptable salts thereof. Preferred indoline derivatives are selected from at least one compound from the group formed by 4-hydroxyindoline, 6-hydroxyindoline and 7-hydroxyindoline, and the physiologically acceptable salts thereof.

Additional coupler components particularly preferred according to the invention are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-yl-phenyl)amino]ethanol, 3-amino-4-(2-methoxyethoxy)-5-methylphenylamine, 1-amino-3-bis-(2-hydroxyethyl)aminobenzene, 2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or the physiologically acceptable salts thereof. Very particularly preferred are 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol, and one of the physiologically acceptable salts thereof.

In addition, the agents according to the invention (i.e., color preparation (K1)) may likewise include at least one direct dye from the group comprising the anionic, nonionic, and/or cationic dyes.

HC Yellow 2, HC Yellow 2, HC Yellow 3, HC Yellow 4, HC Yellow 12, HC Orange 9, Disperse Orange 1, HC Red 0, HC Red 2, HC Red 10, HC Red 11, HC Red 13, HC Red BN, HC Blue 1, HC Blue 11, HC Blue 12, Disperse Blue 2, HC Violet 0, Disperse Violet 0, Disperse Violet 3, and Disperse Black 6, and 1,4-diamino-1-nitrobenzene, 1-amino-3-nitrophenol, 1,4-bis(1-hydroxyethyl)amino-1-nitrobenzene, 2-nitro-3-(1-hydroxyethyl)aminophenol, 0-(1-hydroxyethyl)amino-4,6-dinitrophenol, 3-[(1-hydroxyethyl)amino]-2-nitro-0-methylbenzene, 0-amino-3-(1-hydroxyethyl)amino-4-chloro-1-nitrobenzene, 3-amino-2-nitrophenol, 0-(1'-ureidoethyl)amino-3-nitrobenzene, 7-[(4-amino-2-nitrophenyl)amino]benzoic acid, 5-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

In another particularly preferred embodiment, the agent according to the invention is characterized in that it additionally includes one or more nonionic direct dyes from the group comprising HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitro benzoic acid, and 2-chloro-6-ethylamino-4-nitrophenol.

In addition, anionic direct dyes may also be included which are known by the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

Suitable cationic direct dyes are cationic triphenylmethane dyes, for example Basic Blue 7, Basic Blue 26, Basic Violet 2, and Basic Violet 14, aromatic systems substituted with a quaternary nitrogen group, for example Basic Yellow 57, Basic Red 76, Basic Blue 99, Basic Brown 16, and Basic Brown 17, cationic anthraquinone dyes such as HC Blue 16 (Bluequat B), and direct dyes which include a heterocycle having at least one quaternary nitrogen atom, in particular Basic Yellow 87, Basic Orange 31, and Basic Red 51. The cationic direct dyes, which are marketed under the trademark Arianor, are likewise suitable cationic direct dyes according to the invention. The additional oxidation dye precursors, i.e., developer components and coupler components, which are different from the compounds of groups (A), (B), (C), and (D), and the optionally additionally included direct dyes may be used, for example, in a quantity of 0.0001 to 5.0% by weight, preferably 0.001 to 3.5% by weight, in each case based on the total weight of the agent according to the invention (i.e. of the color preparation (K1)).

Shortly before application, the agent according to the invention (corresponding to color preparation (K1)) is mixed with an oxidizing agent preparation (i.e., oxidizing agent component (K2)). The ready-to-apply oxidative coloring agent is obtained in this way.

For sufficient swelling of the keratin fibers, the ready-to-apply oxidative coloring agent is preferably set to an alkaline pH. The dyeing processes on keratin fibers also customarily proceed in an alkaline environment. However, to protect the keratin fibers and also the skin to the greatest extent possible, setting a pH that is too high is not desirable. It is therefore preferred when the pH of the ready-to-apply agent has a value of 8.0 to 10.5, more preferably 8.7 to 10.3, even more preferably 9.0 to 10.2, and particularly preferably 9.2 to 10.1. The stated pH values are values that have been measured at a temperature of 22° C. with a glass electrode.

The alkalizing agents that are usable according to the invention for setting the preferred pH may be selected from the group, formed by ammonia, alkanolamines, basic amino acids, and inorganic alkalizing agents such as (earth) alkaline metal hydroxides, (earth)-alkaline metal metasilicates, (earth) alkaline metal phosphates, and (earth) alkaline metal hydrogen phosphates. Preferred inorganic alkalizing agents are sodium hydroxide, potassium hydroxide, sodium silicate, and sodium metasilicate. Organic alkalizing agents that are usable according to the invention are preferably selected from monoethanolamine, 2-amino-2-methylpropanol, and triethanolamine. The basic amino acids that are usable as alkalizing agents according to the invention are preferably selected from the group comprising arginine, lysine, ornithine, and histidine, particularly preferably arginine. However, in the testing for the present invention, it has been found that further agents preferred according to the invention are characterized in that they additionally include an organic alkalizing agent. One embodiment of the first subject matter of the invention is characterized in that the agent additionally includes at least one alkalizing agent that is selected from the group comprising ammonia, alkanolamines, and basic amino acids, in particular ammonia, monoethanolamine, and arginine or the acceptable salts thereof. The alkalizing agent(s) together with the oxidation dye precursors are preferably provided in color preparation (K1).

A second subject matter of the present invention relates to a multicomponent packaging unit (kit-of-parts) for oxidatively dyeing keratinic fibers, comprising two preparations (K1) and (K2) that are separately packaged, wherein
  preparation (K1) is an agent of the first subject matter of the invention,
  preparation (K2) includes hydrogen peroxide in an aqueous cosmetic carrier, and
  the mixture of (K1) and (K2) has a pH of 8.0 to 10.5, preferably 8.7 to 10.3, more preferably 9.0 to 10.2, and particularly preferably 9.2 to 10.1.

In one preferred embodiment, hydrogen peroxide itself is used as the aqueous solution in oxidizing agent preparation (K2). The concentration of a hydrogen peroxide solution in color preparation (K2) is determined on the one hand by the regulatory requirements, and on the other hand by the desired effect; 6 to 12% by weight solutions in water are preferably used. Preparations (K2) preferred according to the invention are characterized in that they include 5 to 20% by weight, preferably 1 to 12.5% by weight, particularly preferably 2.5 to 10% by weight, and in particular 3 to 6% by weight, of hydrogen peroxide, in each case based on the total weight of oxidizing agent preparation (K2).

Color preparation (K1) and/or oxidizing agent preparation (K2) may include further bleach enhancers for increasing the lightening effect, for example tetraacetylethylenediamine (TAED), 1,5-diacetyl-2,4-dioxohexahydro-1,3,5-triazine (DADHT), tetraacetylglycoluril (TAGU), N-nonanoyl succinimide (NOSI), n-nonanoyl or isononanoyloxybenzenesulfonate (n- or iso-NOBS), phthalic acid anhydride, triacetin, ethylene glycol diacetate, and 2,5-diacetoxy-2,5-dihydrofuran, as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-containing heterocyclic bleach enhancers, such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

For further increasing the lightening, at least one SiO2 compound such as silicic acid or silicates, in particular water glasses, may additionally be added to color preparation (K1) and/or oxidizing agent preparation (K2). The SiO2 compound may be included in color preparation (K1) and/or in oxidizing agent preparation (K2). It may be preferred according to the invention to use the SiO2 compounds in quantities of 0.05% by weight to 15% by weight, particularly preferably in quantities of 0.15% by weight to 10% by weight, and very particularly preferably in quantities of 0.2% by weight to 5% by weight, in each case based on the total weight of color preparation (K1) or the total weight of oxidizing agent preparation (K2). The stated quantities in each case represent the content of the SiO2 compounds in the agents (not including their water fraction).

The oxidative color change agents (i.e., color preparation (K1) and/or oxidizing agent preparation (K2)) may also include further active substances, auxiliary substances, and additives in order to improve the coloring or lightening power and to set further desired properties in the agent.

The ready-to-apply coloring agents are preferably provided as a liquid preparation, and optionally a further surface-active substance is additionally added to the agents; depending on the field of application, such surface-active substances are referred to as surfactants or as emulsifiers: they are preferably selected from anionic, cationic, zwitterionic, amphoteric, and nonionic surfactants and emulsifiers.

Agents preferred according to the invention are characterized in that the agent includes in addition at least one anionic surfactant. Preferred anionic surfactants are fatty acids, alkyl sulfates, alkyl ether sulfates, and ether carboxylic acids that include 10 to 20 C atoms in the alkyl group and up to 16 glycol ether groups in the molecule.

Agents preferred according to the invention are characterized in that the agent includes in addition at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. A preferred zwitterionic surfactant is known by the INCI name Cocamidopropyl Betaine.

Agents preferred according to the invention are characterized in that the agent includes in addition at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred amphoteric surfactants are N-cocoalkylamino propionate, cocoacylaminoethylamino propionate, and C12-C18 acyl sarcosine.

It has proven advantageous, furthermore, for the agents to include other non-ionogenic surface active substances. Preferred nonionic surfactants are, for example, alkylene oxide adducts to fatty alcohols and fatty acids each with 2 to 30 mol of ethylene oxide per mole of fatty alcohol or fatty acid. Preparations with excellent properties are likewise obtained if they include fatty acid esters of ethoxylated glycerol as the nonionic surfactants.

The nonionic, zwitterionic, or amphoteric surfactants are used in proportions of 0.1 to 45% by weight, preferably 1 to 30% by weight, and very particularly preferably 1 to 15% by weight, based on the total quantity of the ready-to-apply agents.

The ready-to-apply color-changing agents may also include at least one thickener. There are no basic restrictions with regard to these thickeners. Both organic and purely inorganic thickeners may be used.

Suitable thickeners are anionic synthetic polymers, cationic synthetic polymers, naturally occurring thickeners, such as nonionic guar gums, scleroglucan gums, or xanthan gums, gum arabic, gum ghatti, karaya gum, gum tragacanth, carrageenan gum, agar-agar, locust bean gum, pectins, alginates, starch fractions, and derivatives such as amylose, amylopectin, and dextrins, and cellulose derivatives such as methylcellulose, carboxyalkyl celluloses, and hydroxyalkyl celluloses, nonionic synthetic polymers such as polyvinyl alcohol or polyvinylpyrrolidinone, and inorganic thickeners, in particular phyllosilicates such as bentonite, in particular smectites such as montmorillonite or hectorite; as well as inorganic thickeners, in particular phyllosilicates such as, for example, bentonite, in particular smectites, such as montmorillonite or hectorite.

Furthermore, it has proven to be advantageous when the coloring agents, in particular when they additionally include hydrogen peroxide, include at least one stabilizer or complexing agent. Especially preferred stabilizers are phenacetin, alkali benzoates (sodium benzoate), and salicylic acid. Furthermore, all complexing agents in the state of the art can be used. Complexing agents preferred according to the invention are nitrogen-containing polycarboxylic acids, particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

Further, the agents of the invention can include other active substances, auxiliary substances, and additives, such as, for example, fatty alcohols, nonionic polymers such as, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or noncrosslinked polyalkylsiloxanes (such as dimethicones or cyclomethicones), polyarylsiloxanes, and/or polyalkylarylsiloxanes, particularly polysiloxanes with organofunctional groups, such as substituted or unsubstituted amines (amodimethicones), carboxyl, alkoxy, and/or hydroxyl groups (dimethicone copolyols), linear polysiloxanes(A)-polyoxyalkylene (B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate-vinylpyrrolidinone copolymers quaternized with diethylsulfate, vinylpyrrolidinone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair conditioning compounds such as phospholipids, for example, lecithin and kephalins; perfume oils, dimethyl isosorbide, and cyclodextrins; fiber structure improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids, and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ether, carbonates, hydrogen carbonates, guanidines, ureas, and primary, secondary, and tertiary phosphates; opacifiers such as latex, styrene/PVP, and styrene/acrylamide copolymers; pearlescent agents such as ethylene glycol mono- and distearate and PEG-3 distearate; pigments and propellants such as propane-butane mixtures, N2O, dimethyl ether, CO2, and air. The selection of these additional substances is made by the skilled artisan according to the desired properties of the agents. In regard to other facultative components and the employed amounts of said components, reference is made expressly to relevant handbooks known to the skilled artisan. The additional active substances and auxiliary substances are preferably used in the agents according to the invention in each case in quantities of 0.0001 to 25% by weight, in particular 0.0005 to 15% by weight, based on the total weight of the color preparation (K1) and/or the oxidizing agent preparation (K2).

The agents according to the invention show extremely good suitably for dyeing keratinic fibers; the dyed fibers have very good wash fastness.

A further subject matter of the present invention therefore relates to the use of an agent of the first subject matter of the invention for improving the wash fastness of the colorings obtained with this agent.

A further subject matter of the present invention also relates to the use of an agent of the second subject matter of the invention for improving the wash fastness of the colorings obtained with this agent.

The statements concerning the agent according to the invention apply mutatis mutandis with regard to further embodiments of the kit according to the invention and the uses according to the invention.

EXAMPLES a. Production of the Coloring Agents
The following color creams were produced:

| Color cream (quantity: 100 g) | V1 (comparison) | E1 (invention) |
|---|---|---|
| 4,5-Diamino-1-(2-hydroxyethyl)-1H-pyrazole (sulfate) | 4.80 g<br>0 mmol | 4.80 g<br>20 mmol |
| p-aminophenol (hydrochloride) | 1.46 g<br>10 mmol | 1.46 g<br>10 mmol |
| 2,6-bis(2'-hydroxyethylamino)-1-methylbenzene | 8.42 g<br>40 mmol | 4.21 g<br>20 mmol |
| 2-Methylresorcinol | — | 2.48 g<br>20 mmol |
| Hydrenol D (cetearyl alcohol) | 8.5 g | 8.5 g |
| Technical Lorol (C12-C18 fatty | 2.0 g | 2.0 g |
| Texapon NSO (sodium laureth sulfate, approx. 27.5% by weight active substance) | 20.0 g | 20.0 g |
| Dehyton K (cocoamidopropyl betaine, approx. 30% by weight active substance) | 12.5 g | 12.5 g |
| Sodium sulfite | 1.0 g | 1.0 g |
| Ammonium sulfate | 1.0 g | 1.0 g |
| Water (distilled) | ad 100 g | ad 100 g |

The color creams V1 and E1 were in each case mixed in a 1:1 weight ratio with the following oxidizing agent preparation.

| Oxidizing agent preparation (quantity: 100 g) | OX |
|---|---|
| Dipicolinic acid | 0.1 g |
| Sodium pyrophosphate | 0.03 g |
| Turpinal SL (1-hydroxyethane-1,1-diphosphonic acid, 58-61% by weight active substance) | 1.50 g |
| Texapon N28 (sodium laureth sulfate, at least 26.5% by weight active substance) | 2.00 g |
| Aerysol 22 (Acrylates/Steareth-20 Methacrylate Copolymer, active substance 29.5-30.5% by weight) | 0.60 g |
| Hydrogen peroxide (50% aqueous solution) | 6.0 g |
| Sodium hydroxide solution (45% aqueous solution) | 0.80 g |
| Water (distilled) | ad 100 g |

The pH was set to 10.0 by adding a 25% aqueous ammonia solution.

1.2 Application

The ready-to-apply oxidative coloring agents (V1+OX, E1+OX) produced in this way were each applied to three hair strands (Kerling, Euronaturhaar white) and allowed to act for a period of 30 minutes at room temperature. The strands were then rinsed with lukewarm tap water for one minute and dried in a cold air stream. Each hair strand was subsequently colorimetrically measured at four different points in each case (two on the front side of the strand, two on the rear side of the strand). The average was formed from the four measured values.

1.3 Determination of Wash Fastness

To determine the wash resistance, a 2% standard shampoo solution was filled to the top fill mark in an ultrasonic bath. The hair strands to be treated were completely immersed therein and treated with ultrasound. After a period of time corresponding to the equivalent of 12 repeated hair washings, the strands were removed from the ultrasonic bath and dried in a cold air stream.

Each hair strand was subsequently once again colorimetrically measured at four different points in each case (two on the front side of the strand, two on the rear side of the strand). The average was formed from the four measured values.

Based on the obtained L*a*b* values, in each case the color difference (ΔE value) between the unwashed strands and the strands washed in a defined manner was determined, using the CIELAB2000 formula. The ΔE values were used for determining the wash fastness; the larger the ΔE values in question, the lower the wash fastness rating. Each ready-to-apply oxidative coloring agent was intensely colored on three strands.

The following ΔE values were obtained:
Wash fastness after 12 hair washings

|  | V1 + OX | E1 + OX |
|---|---|---|
| ΔE values | 6.78 | 4.56 |

The hair strands treated with the oxidative coloring agent according to the invention (E1+OX) showed a smaller ΔE value, and thus, improved wash fastness, compared to the comparative formulations (V1+OX).

1.4 Determination of Light Fastness

After the dyeing and colorimetric measurement, the dried strands were clamped in metal holders and then placed in a UV weathering test apparatus. The strands were then irradiated in a defined manner with UV light for a period of 98 hours (50 W/m$^2$). The strands were subsequently removed from the measuring device and colorimetrically measured once again.

Based on the obtained L*a*b* values, in each case the color difference (ΔE value) between the unexposed strands and the strands exposed in a defined manner was determined, using the CIELAB2000 formula. The ΔE values were used for determining the light fastness; the larger the ΔE values in question, the lower the light fastness rating.

The following ΔE values were obtained:

Light fastness after an exposure period of 98 hours

|  | V1 + OX | E1 + OX |
|---|---|---|
| ΔE values | 31.71 | 20.10 |

The hair strands treated with the oxidative coloring agent according to the invention (E1+OX) showed a smaller ΔE value, and thus, improved light fastness, compared to the comparative formulations (V1+OX).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for oxidatively dyeing keratinic fibers, including in a cosmetic carrier
   (A) 4,5-diamino-1-(2-hydroxyethyl)-1H-pyrazole and/or one of the physiologically acceptable salts thereof as developer,
   (B) p-aminophenol and/or one of the physiologically acceptable salts thereof as developer,
   (C) 2,6-bis(2'-hydroxyethylamino)-1-methylbenzene and/or one of the physiologically acceptable salts thereof as coupler, and
   (D) at least one m-dihydroxybenzene derivative selected from the group consisting of resorcinol, 2-methylresorcinol, and/or 4-chlororesorcinol as coupler,
   wherein a molar ratio (C)/(D), defined as the molar ratio of all couplers of group (C) included in the agent to all couplers of group (D) included in the agent has a value of at least 0.5 and has a maximum value of 1.5.

2. The agent according to claim 1, wherein a molar ratio (A)/(B), defined as the molar ratio of all developers of group (A) included in, the agent to all developers of group (B) included in the agent, has a value of at least 1.

3. The agent according to claim 2, wherein the molar ratio (A)/(13) has a maximum value of 3.

4. The agent according to claim 1, including (D) 2-methylresorcinol as coupler.

5. The agent according to claim 1, including (D) resorcinol as coupler.

6. The agent according to claim 1, including (D) 4-chlororesorcinol as coupler.

7. The agent according to claim 1, wherein a molar ratio [(A)+(B)]/[(C)+(D)], defined as the molar ratio of all developers of groups (A) and group (B) included in the agent to all couplers of groups (C) and (D) included, in the agent, has a value of at least 0.4.

8. The agent according to claim 7, wherein the molar ratio [(A)+(B)]/[(C)+(D)] has a maximum value of 0.95.

9. The agent according to claim 1, wherein the developer(s) of group (A) are included in an overall molality of 0.10 to 0.50 mol/kg based on the total weight of the agent.

10. The agent according to claim 1, wherein the couplers of groups (C) and (D) are included in an overall molality of 0.10 to 1.00 mol/kg based on the total weight of the agent.

11. A multicomponent packaging unit (kit-of-parts) for oxidatively dyeing keratinic fibers, comprising two preparations (K1) and (K2) that are separately packaged, wherein
   preparation (K1) is an agent according to claim 1,
   preparation (K2) includes hydrogen peroxide in an aqueous cosmetic carrier, and
   the mixture of (K1) and (K2) has a pH of 8.0 to 10.5.

* * * * *